Oct. 6, 1959 G. MERRILL Plant Pat. 1,870
PEACH TREE
Filed Aug. 11, 1958
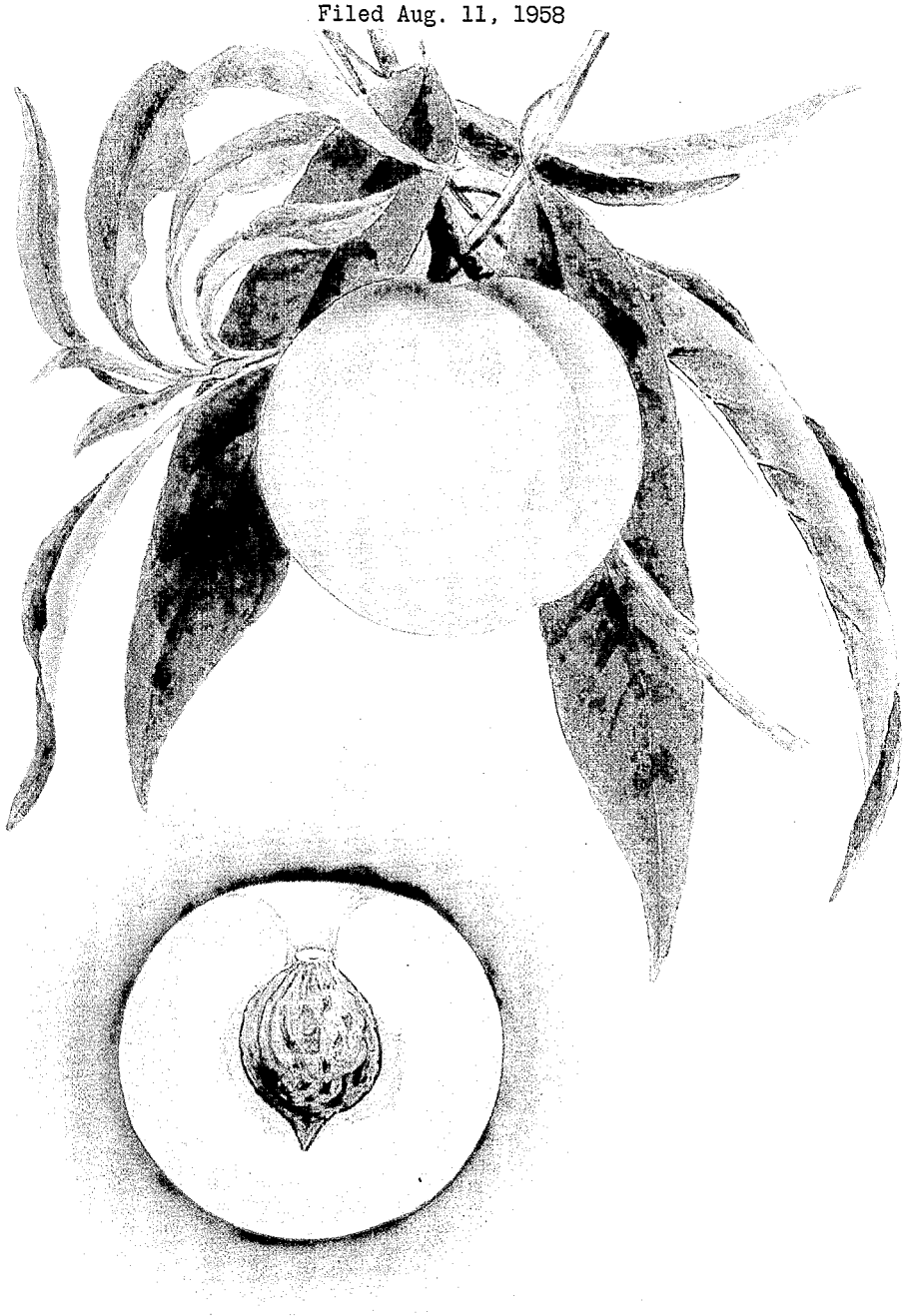
WITNESS
Addison E. Avery
INVENTOR
Grant Merrill
HUEBNER & WORREL
BY Richard M. Worrel
ATTY.

United States Patent Office

Plant Pat. 1,870
Patented Oct. 6, 1959

1,870

PEACH TREE

Grant Merrill, Red Bluff, Calif.

Application August 11, 1958, Serial No. 754,507

1 Claim. (Cl. 47—62)

This invention relates to a new and distinct variety of peach tree bearing large highly colored, firm, yellow fleshed, freestone peaches.

A distinguishing feature of this variety is that the fruit ripens uniformly throughout the tree with relatively short ripening and picking period, and ripens about five days ahead of Elberta (unpatented).

In comparison with Merrill Gemfree (Plant Patent No. 1,409) which it most nearly resembles, the instant variety ripens about forty five days later and the skin is nearly as red, but the red is of brighter color and the flesh is completely free from the pit.

I originated the present variety of peach tree on my farm near Red Bluff, Tehama County, California in the following manner:

Seeds were planted for four generations of open pollinated blossoms ($F_4$) starting with J. H. Hale (unpatented) and selecting each time for high color, firmness and side of fruit, along with good tree producing characteristics. In the fourth generation ($F_4$) this selection first fruited in July, 1954, and was an improvement over its parents. In the spring of 1956, several peach trees of the Merrill June variety (Plant Patent No. 869) growing on my farm near Lamont, Kern County, California were grafted to this new variety. In July 1958, these grafts bore fruit and it has been observed that the asexually reproduced trees possess the same characteristics as the original ($F_4$) seedling.

The drawing is a water color painting of several characteristic twigs and leaves of the instant variety as they appear during picking season and showing a mature fruit borne by one of the twigs. The drawing also shows a fruit of the instant variety divided on its suture plane to disclose flesh coloration and pit form and coloration.

Referring now more specifically to the pomological details of this new and distinct variety of peach tree, the following is an outline description thereof; all major color plate identifications being by reference to Maerz and Paul Dictionary of Color:

*Tree*

Medium size, medium vigorous, medium upright, medium dense, vase formed by pruning, productive, regular bearer.

Trunk: Medium stocky, medium shaggy. Color—gray.
Branches: Older branches—gray; younger branches—brown. Lenticels—medium size, medium quantity.
Leaves (selected from midportion of vigorous unbranched terminal shoot 18" to 24" long):
*Length.*—5¾" to 6⅝", average 6⅛".
*Width.*—1 1/16" to 1½", average 1 5/16". Medium size.
*Shape.*—Lanceolate, tip acuminate.
*Thickness.*—Medium thick.
*Color.*—Upper surface of leaves green (26–L–1, plus yellow). Under side lighter green (21–J–6).

Heavy midrib on underside, lighter green (17–I–1).
*Class* (Meader and Blake: Proceedings Am. Soc. Hort. Sci. vol 27, page 206).—2 and 3. Width-length ratio—.21. Apex angle—26° to 29°, average 28°. Base angles—75° to 78°, average 77°.
*Margin.*—Crenate.
*Petiole.*—Medium length, medium slender.
*Glands.*—Reniform, two to four, average three, opposite and alternate, medium size, green to yellow, mostly on petiole, few on base of leaves.
*Stipules.*—At base of leaf and dropping off early.
Flower buds: Medium size, medium length, truncate to obtuse, plump, free, pubescent.
Flowers: Medium early as compared with other varieties, about with Elberta, small size, pink in color. Pollen abundant.

*Fruit*

Maturity when described, eating ripe.

Size: Fairly uniform.
*Axial diameter.*—2½" to 2¾", average 2⅝".
*Transverse in suture plane.*—2⅝" to 3", average 2 13/16".
*At right angles to suture plane.*—2⅝" to 3", average 2 13/16".
Form: Globose to slightly compressed axially.
*Suture.*—Inconspicuous to distinct, extends from base to beyond, but discontinues at apex. Has slight depression beyond pistil point.
*Ventral surface.*—Rounded slightly, lipped slightly to distinctly.
*Cavity.*—Somewhat abrupt, elongated in suture plane, with suture showing on both sides. Depth ½". Breadth 9/16" to ⅝", average 19/32". Markings—under color yellow with red blush from none to 100%.
*Base.*—Retuse.
*Apex.*—Rounded.
*Pistil point.*—None to slight, apical.
*Stem.*—Length average ⅜", diameter ⅛", few adhere to stone.
*Skin.*—Medium thick, medium tender, free from flesh when soft ripe. Tendency to crack—none. Color—yellow (9–L–5) to yellow (9–J–8) to moderate blush (4–L–6) to heavy blush (7–L–6) with blush covering half or more of the fruits and increasing as the fruit ripens, but flesh remains firm while very red. Down—moderate, short, does not roll up when rubbed.
Flesh: Color yellow, base color (9–K–4) to yellow near the skin (9–L–7 to –9) and with considerable red at the stone (2–L–8).
*Surface of pit cavity.*—Red with conspicuous pink and red fibers.
*Amygdalin.*—Moderate.
*Juice.*—Moderate.
*Texture.*—Firm, fine, meaty.
*Fibers.*—Moderate in amount.
*Ripens.*—Evenly and uniformly throughout the tree.
*Flavor.*—Mild subacid.
*Aroma.*—Moderate.
*Eating quality.*—Good.
Stone: Completely free from flesh. Fibers, moderate in amount.
*Size.*—Length—1 7/16" to 1 9/16", average 1 15/32". Breadth—1 1/16" to 1 3/16", average 1⅛". Thickness—13/16" to 15/16", average ⅞".
*Form.*—Ovate, tip cuspidate, size—medium large.
*Base.*—Straight to slightly oblique.
*Apex.*—Strongly cuspidate.

*Hilum.*—Oval.

*Sides.*—Mostly equal, few unequal.

*Surface.*—Mostly pitted, some furrows near base, sometimes along ventral and sometimes along dorsal side. Ventral edge—moderately broad with narrow furrows, relatively short and interrupted, varying considerably. Dorsal edge—usually two ridges and one groove, usually interrupted.

*Color.*—Brown (7–A–12) to purple (6–E–4) with a tendency of more purple toward base and along ventral side, sometimes on dorsal, sometimes extending over entire surface.

Use: Market, local, dessert, culinary and long distance shipping.

Keeping quality: Good.

Shipping quality: Good.

It is to be understood that normal variations in the described characteristics of the new variety peach tree incident to cultural and environmental changes must be expected. However, the characteristics are consistently maintained through asexual reproduction and no variations therein have been observed under the ecological conditions prevailing on my farms at Red Bluff, Tehama County, California and near Lamont, Kern County, California.

Having illustrated and described my new invention, what I claim as new and desire to secure by Letters Patent is:

A new and distinct variety of peach tree substantially as described and illustrated, characterized by the production of large, highly colored, firm, yellow fleshed freestone peaches which ripen uniformly throughout the tree approximately five days ahead of the Elberta (unpatented), said peaches being most nearly similar to those of Merrill Gemfree (Plant Patent No. 1,409), but being an improvement thereover by ripening approximately 45 days later, having a skin color of somewhat brighter red, and by the flesh being completely free from the pit.

No references cited.